United States Patent
Choi et al.

(10) Patent No.: US 11,333,801 B2
(45) Date of Patent: May 17, 2022

(54) MINIATURE IMAGE RELAY ENDOSCOPY PROBE AND MULTI-PHOTON ENDOSCOPY INCLUDING THE SAME

(71) Applicant: Research & Business Foundation Sungkyunkwan University, Suwon-si (KR)

(72) Inventors: Myunghwan Choi, Suwon-si (KR); Jisoo Han, Seoul (KR); Sungho Lee, Daejeon (KR); Pyonggang Choi, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 181 days.

(21) Appl. No.: 16/555,295

(22) Filed: Aug. 29, 2019

(65) Prior Publication Data
US 2020/0069158 A1    Mar. 5, 2020

(30) Foreign Application Priority Data
Aug. 30, 2018    (KR) .................. 10-2018-0102483

(51) Int. Cl.
| | | |
|---|---|---|
| G02B 1/10 | (2015.01) | |
| A61B 1/00 | (2006.01) | |
| G02F 1/35 | (2006.01) | |
| G02B 3/00 | (2006.01) | |

(52) U.S. Cl.
CPC ............ *G02B 1/10* (2013.01); *A61B 1/00096* (2013.01); *A61B 1/00163* (2013.01); *A61B 1/00186* (2013.01); *A61B 1/00195* (2013.01); *G02B 3/0087* (2013.01); *G02F 1/3526* (2013.01)

(58) Field of Classification Search
CPC ............ A61B 1/00096; A61B 1/00163; G02B 3/0087
See application file for complete search history.

(56) References Cited

U.S. PATENT DOCUMENTS

| | | | | |
|---|---|---|---|---|
| 5,995,294 A | * | 11/1999 | West | .................... G02B 3/0087 359/642 |
| 6,327,493 B1 | * | 12/2001 | Ozawa | ................. A61B 5/0073 348/45 |
| 2009/0012406 A1 | | 1/2009 | Llewellyn et al. | |
| 2009/0054791 A1 | | 2/2009 | Flusberg et al. | |
| 2010/0292539 A1 | * | 11/2010 | Lankenau | .......... G01B 9/02091 600/167 |

FOREIGN PATENT DOCUMENTS

| | | |
|---|---|---|
| KR | 10-2017-0016773 A | 2/2017 |
| KR | 10-2018-0029605 A | 3/2018 |

OTHER PUBLICATIONS

Korean Office Action dated Jul. 22, 2021 in counterpart Korean Patent Application No. 10-2018-0102483 (5 pages in Korean).

* cited by examiner

*Primary Examiner* — Aaron B Fairchild
(74) *Attorney, Agent, or Firm* — NSIP Law (57) ABSTRACT

Provided are a miniature endoscopic probe and a multi-photon endoscopy including the same.

19 Claims, 5 Drawing Sheets

MINIATURE IMAGE RELAY ENDOSCOPY PROBE AND MULTI-PHOTON ENDOSCOPY INCLUDING THE SAME

CROSS REFERENCE TO RELATED APPLICATIONS

This application claims the benefit under 35 USC 119(a) of Korean Patent Application No. 10-2018-0102483 filed on Aug. 30, 2018 in the Korean Intellectual Property Office, the entire disclosure of which is incorporated herein by reference for all purposes.

FIELD

The present disclosure relates to a miniature endoscopic probe and a multi-photon endoscopy including the same.

BACKGROUND

A multi-photon microscopy is a non-linear optical phenomenon-based microscopy that includes multi-photon absorption, second-harmonic generation, and the like, and due to high tissue permeability, the multi-photon microscopy has been actively used for small animal bioimaging researches including brain science.

An endoscopy is a device for non-invasively observing the inside of living organs, such as the digestive organs, respiratory organs, etc. and has been widely used in such clinical and experimental. Optical imaging techniques, including the multi-photon microscopy, are difficult to be used in deep tissues due to the limitations of the light transmittance of the tissues, and a miniature endoscopy solves the problem by a non-invasive or minimal-invasive method. For example, when non-invasively observing cancer in the inner wall of the mouse's colon, a miniature endoscopic probe capable of transmitting image information is inserted through the anus and the image information of the inner wall is measured. As the minimally invasive method, it has been reported an example in which the miniature endoscopy is inserted in rats to observe deep structures, such as the hippocampus in the brain, or in humans, the miniature endoscopy is inserted in the muscle layer.

Gradient index lenses (GRIN lenses) have been widely used to construct the miniature endoscopy. The GRIN lens has high optical performance in a small form factor and is easily applied and used to existing microscopies. Recently, in the field of brain science, multi-photon endoscopy, which combines a miniature endoscopy with a multi-photon microscopy, has observed minimal-invasively the activity of brain cells in small animals. Although it is important to collect light from a sample efficiently in order to obtain high-dimensional spatiotemporal information, conventional GRIN lenses generally have a small numerical aperture (NA) of about 0.1 to 0.6.

In the multi-photon microscopy, the use of additional optical fibers, light collection using reflectors, and a configuration of embedding a beam splitter in an objective lens have been proposed to increase light collection efficiency, but this method does not help in light collection in multi-photon endoscopy situations where miniature endoscopies are used.

US Patent Publication No. 2009-0012406, which is the background technology of the present disclosure, discloses biomedical cell level imaging system and method. Specifically, US Patent Publication No. 2009-0012406 discloses an optical probe including a light transmitting source to living tissues and a light emitting collector for sensing a signal induced from the tissue, in which the optical probe includes a gradient index lens (GRIN lens) minute endoscopy optical probe.

DISCLOSURE OF THE INVENTION

Problems to be Solved by the Invention

An object of the present disclosure is to solve the above-mentioned problems of the related art, and to overcome limitations that in the case of using a conventional gradient index lens in a multi-photon endoscopy, due to a low numerical aperture of the gradient index lens, a signal to noise ratio is reduced and it is difficult to obtain a clear image.

However, the technical problem to be achieved by the embodiments of the present disclosure is not limited to the technical problems as described above, and other technical problems may exist.

Means for Solving the Problems

As a technical means for achieving the above technical problem, a first aspect of the present disclosure provides a miniature endoscopic probe including a gradient index lens (GRIN lens) formed with a reflective waveguide, in which the reflective waveguide is formed on a side surface of the GRIN lens.

According to an embodiment, the reflective waveguide may be formed by light reflection coating on a side surface of GRIN lens, but is not limited thereto.

According to an embodiment, the reflective waveguide may include a metal selected from the group consisting of silver, gold, aluminum, tin, copper, brass, bronze, molybdenum, chromium, rhodium, platinum and combinations thereof or a dielectric material selected from the group consisting of $SiO_2$, $TiO_2$, $Ta_2O_5$, $MgF_2$, $Al_2O_3$ and combinations thereof, but is not limited thereto.

According to an embodiment, the light reflection coating may be performed by a method selected from the group consisting of vacuum deposition, sputter deposition, lithography, solution-based reductive coating, and combinations thereof, but is not limited thereto.

According to an embodiment, the miniature endoscopic probe may further include a protective layer formed on the reflective waveguide, but is not limited thereto.

According to an embodiment, the protective layer may be formed by polymer coating, but is not limited thereto.

According to an embodiment, the polymer coating may include parylene coating, but is not limited thereto.

According to an embodiment, the protective layer may include an alloy steel tube, but is not limited thereto.

According to an embodiment, the alloy steel tube may include a steel selected from the group consisting of stainless steel, chromium steel, nickel steel, nickel-chromium steel, chromium-molybdenum steel, manganese steel, chromium-vanadium steel, tungsten steel and combinations thereof, but is not limited thereto.

A second aspect of the present disclosure provides a multi-photon endoscopy, including the miniature endoscopic probe; and a multi-photon microscopy.

According to an embodiment, the miniature endoscopic probe may be fixed and coupled onto a focal plane of the multi-photon microscopy, but is not limited thereto.

According to an embodiment, the multi-photon endoscopy may further include one selected from the group consisting of a non-descanned detector, a femtosecond pulsed laser, a galvo-scanner, and combinations thereof, but is not limited thereto.

According to an embodiment, the multi-photon microscopy may include an objective lens, and the objective lens may have a numerical aperture larger than that of miniature endoscopic probe, but is not limited thereto.

According to an embodiment, the objective lens may have a numerical aperture of 0.2 to 1.5, but is not limited thereto.

According to an embodiment, the miniature endoscopic probe may have a numerical aperture of 0.17 to 0.8, but is not limited thereto.

The above-mentioned technical solutions are merely exemplary and should not be construed as limiting the present disclosure. In addition to the above-described exemplary embodiments, additional embodiments may exist in the drawings and detailed description of the invention.

Effects of the Invention

According to the technical solutions of the present disclosure described above, the miniature endoscopic probe of the present disclosure includes the reflective waveguide formed by light reflection coating on the GRIN lens, thereby improving collection efficiency of the miniature endoscopic probe. Through this, the multi-photon endoscopy including the miniature endoscopic probe according to the present disclosure may acquire a clearer image in the same image measurement situation, or may acquire the same level of image with a low light source. In addition, it is possible to reduce the effects of photo-toxicity and photo-bleaching due to long-term shooting by using the low light source. The multi-photon endoscopy according to the present disclosure may be particularly useful in the measurement of a living body image.

The coating method of the miniature endoscopic probe according to the present disclosure may simplify the process and effectively improve the efficiency of the miniature endoscopic probe. Therefore, the miniature endoscopic probe of the present disclosure has an advantage of enabling mass production and having low cost.

The patent or application file contains a least one drawing executed in color. Copies of this patent or patent application publication with color drawing(s) will be provided by the Office upon request and payment of the necessary fee.

DETAILED DESCRIPTION

Hereinafter, embodiments of the present disclosure will be described in detail so as to be easily implemented by those skilled in the art, with reference to the accompanying drawings. However, the present disclosure may be embodied in many different forms and are not limited to embodiments described herein. In addition, a part not related with a description is omitted in order to clearly describe the present disclosure in the drawings and throughout the specification, like reference numerals designate like elements.

Further, throughout the specification, when it is described that a certain part is "connected" with another part, it means that the certain part may be "directly connected" with the another part and a third part may be interposed therebetween as well.

Throughout this specification, it will be understood that when a member is referred to as being "on", "upper", "top of", "under", "below", "bottom of" another member, it can be directly on the other member or intervening members may also be present.

Throughout the specification, a case where a part "comprises" an element will be understood to imply the inclusion of stated elements but not the exclusion of any other elements unless explicitly described to the contrary.

The terms "about", "substantially", and the like to be used in this specification are used as a numerical value or a value close to the numerical value when inherent manufacturing and material tolerances are presented in the stated meaning, and used to prevent an unscrupulous infringer from unfairly using disclosed contents in which precise or absolute numerical values are mentioned to help in the understanding of the present disclosure. Throughout this specification, the term of a degree used "step (of~)" or "step of~" does not mean "step for".

Throughout this specification, the term "combinations thereof" included in the expression of the Markush form means one or more mixtures or combinations selected from the group consisting of components described in the expression of the Markush form, and means to include at least one selected from the group consisting of the components.

Throughout the present specification, "A and/or B" means "A and B, or A or B".

Throughout this specification, the term "side surface" means a surface other than a bottom surface and a top surface of surfaces of a three-dimensional figure.

Hereinafter, a miniature endoscopic probe and a multi-photon endoscopy including the same of the present disclosure will be described in detail with reference to exemplary embodiments, Examples, and drawings. However, the present disclosure is not limited to these exemplary embodiments, Examples and drawings.

As a technical means for achieving the above technical problem, a first aspect of the present disclosure provides a miniature endoscopic probe including a gradient index lens (GRIN lens) formed with a reflective waveguide, in which the reflective waveguide is formed on a side surface of the GRIN lens.

Figure 1:
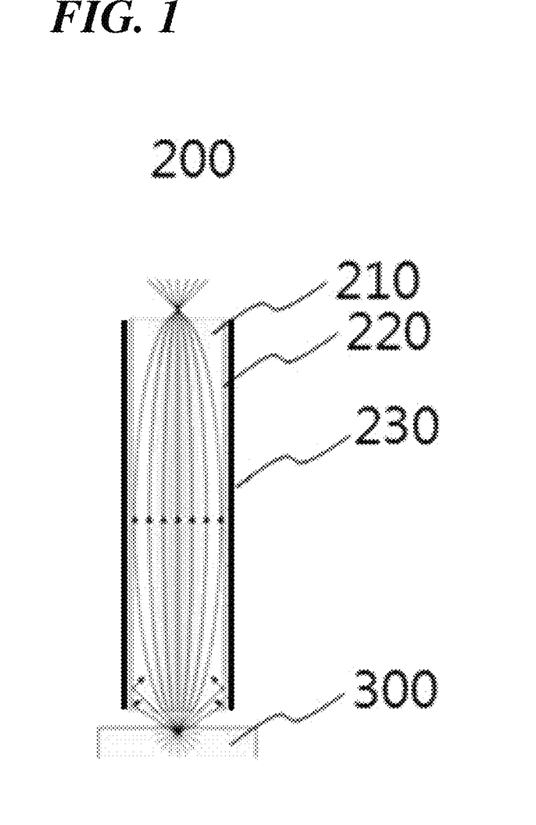
FIG. 1 is a schematic diagram illustrating a miniature endoscopic probe according to an embodiment.
Figure 2:
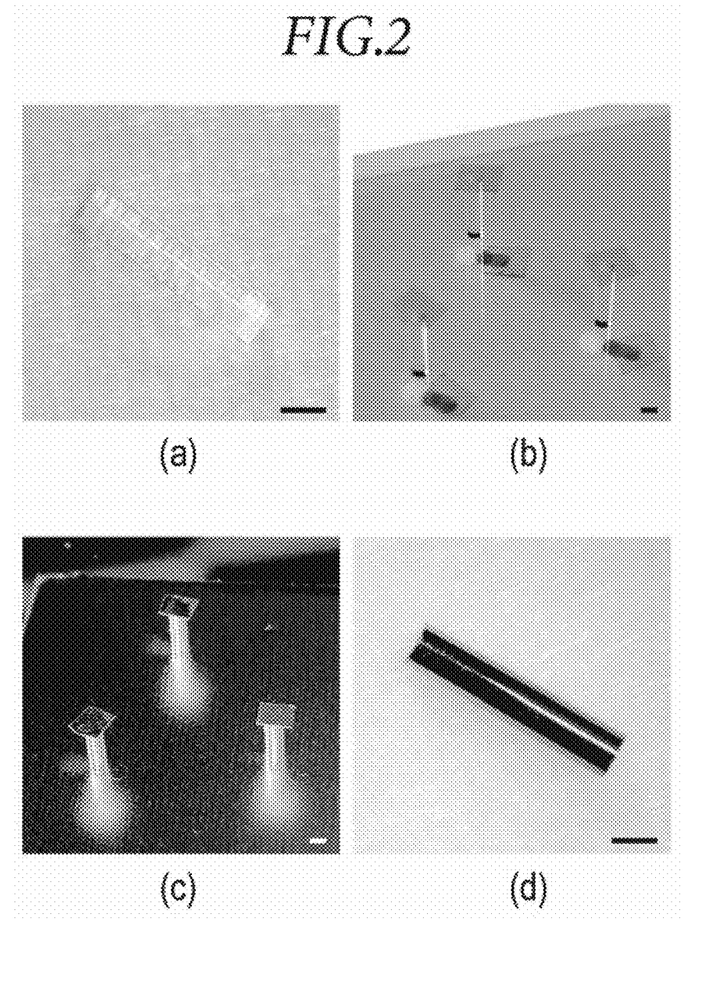
FIGS. 2A to 2D are photographs of a process of forming a reflective waveguide by coating a metal or dielectric material on the side of a gradient index lens of the miniature endoscopic probe according to the embodiment.

FIG. 1 is a schematic diagram illustrating a miniature endoscopic probe according to an embodiment. Referring to FIG. 1, a miniature endoscopic probe 200 according to an embodiment includes a gradient index lens (GRIN lens) 210 and a reflective waveguide 220.

The GRIN lens means glass which has a predetermined gradient refractive index and acts as a lens. The gradient refractive index is formed by ion exchange of glass by diffusion or ion exchange of a porous gel obtained by a sol-gel method. The GRIN lens is generally used to construct an endoscopic probe because it has excellent optical performance in a small form factor and is easy to integrate with an existing microscopy. In addition, the GRIN lens-based endoscopic probe may be designed to include a singlet, a doublet, a triplet, and the like.

A waveguide means a path that can efficiently transmit an electromagnetic wave, and a reflective waveguide means a path that transmits light through light reflection.

According to an embodiment, the reflective waveguide 220 may be formed by a light reflection coating on the side surface of the GRIN lens 210, but is not limited thereto. The light reflection coating means that when light is reflected from the surface of the material, light having a numerical aperture or more is minimized to be transmitted or absorbed, and the reflected light is formed on the surface of the material to be continuously guided.

The GRIN lens-based multi-photon endoscopy has been widely used for studying the behavior of internal organ cells through minimally invasive surgical holes in vivo. Efficient collection of light is required for imaging measurement, but the collection efficiency using conventional endoscopic probe s is limited. In order to recognize and solve these problems, the present inventors confirmed that the collection efficiency of the miniature endoscopic probe 200 may be improved by using the reflective waveguide 220 formed when the light reflection is formed on the side surface of the GRIN lens 210. The miniature endoscopic probe 200 is used to improve the collection efficiency about two times in practical applications such as imaging of fluorescent neurons in the brain and second harmonic generation (SHG)-based imaging of the skeletal muscle. Through this, the multi-photon endoscopy 10 including the miniature endoscopic probe 200 according to the present disclosure may acquire a clearer image in the same image measurement situation, or may acquire the same level of image with a low light source. In addition, it is possible to reduce the effects of photo-toxicity and photo-bleaching due to long-term shooting by using the low light source. The multi-photon endoscopy 10 according to the present disclosure may be particularly useful in the measurement of a living body image.

FIGS. 2A to 2D are photographs of a process of forming the reflective waveguide 220 by light reflection coating a metal or dielectric material on the side surface of the gradient index lens 210 of the miniature endoscopic probe 200 according to the embodiment. Referring to FIGS. 2A to 2D, the bottom and top surfaces of the GRIN lens 210 are sealed with a polyimide tape, and then only the side surface of the GRIN lens 210 may be formed with light reflection by a vacuum deposition method. After the light reflection coating is completed, the polyimide tape is separated.

According to an embodiment, the reflective waveguide may include a metal selected from the group consisting of silver, gold, aluminum, tin, copper, brass, bronze, molybdenum, chromium, rhodium, platinum and combinations thereof or a dielectric material selected from the group consisting of $SiO_2$, $TiO_2$, $Ta_2O_5$, $MgF_2$, $Al_2O_3$ and combinations thereof, but is not limited thereto. Preferably, the reflective waveguide may include silver and chromium. First, the GRIN lens 210 may be formed with silver, and then chromium may be additionally formed on the formed silver surface to protect the silver coating.

Since the dielectric material is capable of reflecting or transmitting light at a specific wavelength band by using interference of light, the dielectric material may be used as a reflective waveguide having a light reflection coating characteristic. Since the metal also has a high reflectance, the metal may be used as a reflective waveguide having the light reflection coating characteristic.

According to an embodiment, the light reflection coating may be performed by a method selected from the group consisting of vacuum deposition, sputter deposition, lithography, solution-based reductive coating, and combinations thereof, but is not limited thereto. Preferably, the light reflection coating may be performed by a vacuum deposition method. The vacuum deposition refers to a process of heating a metallic or nonmetallic material in a vacuum to deposit the vapor on the surface of an object in a thin film form or by forming a film by a chemical method to adhere the film.

According to an embodiment, the miniature endoscopic probe 200 may further include a protective layer 230 formed on the reflective waveguide 220, but is not limited thereto. The protective layer 230 may be further formed on the reflective waveguide 220 to ensure high stability when the endoscopic probe 200 is used for a long time.

According to an embodiment, the protective layer 230 may be formed by polymer coating, but is not limited thereto.

According to an embodiment, the polymer coating may include parylene coating, but is not limited thereto. The parylene coating is a coating method which has been often used as a surface protective coating of products requiring corrosion resistance, water resistance, insulation resistance, drug resistance, and chemical resistance. Unlike general surface protection coating methods such as immersion and spray methods used for coating of urethane, silicone, epoxy, and teflon, the parylene coating uses a chemical vapor deposition method, thereby ensuring a constant thickness regardless of the shape of the product. In addition, the parylene coating may selectively control a thickness to a micro unit, and there is an advantage to minimize the mechanical stress of the product.

The protective layer 230 may include a material selected from the group consisting of, for example, urethane, silicone, epoxy, and combinations thereof, but is not limited thereto.

According to an embodiment, the protective layer 230 may include an alloy steel tube, but is not limited thereto.

According to an embodiment, the alloy steel tube may include a steel selected from the group consisting of stainless steel, chromium steel, nickel steel, nickel-chromium steel, chromium-molybdenum steel, manganese steel, chromium-vanadium steel, tungsten steel and combinations thereof, but is not limited thereto.

A second aspect of the present disclosure provides a multi-photon endoscopy, including the miniature endoscopic probe; and a multi-photon microscopy.

Figure 3:
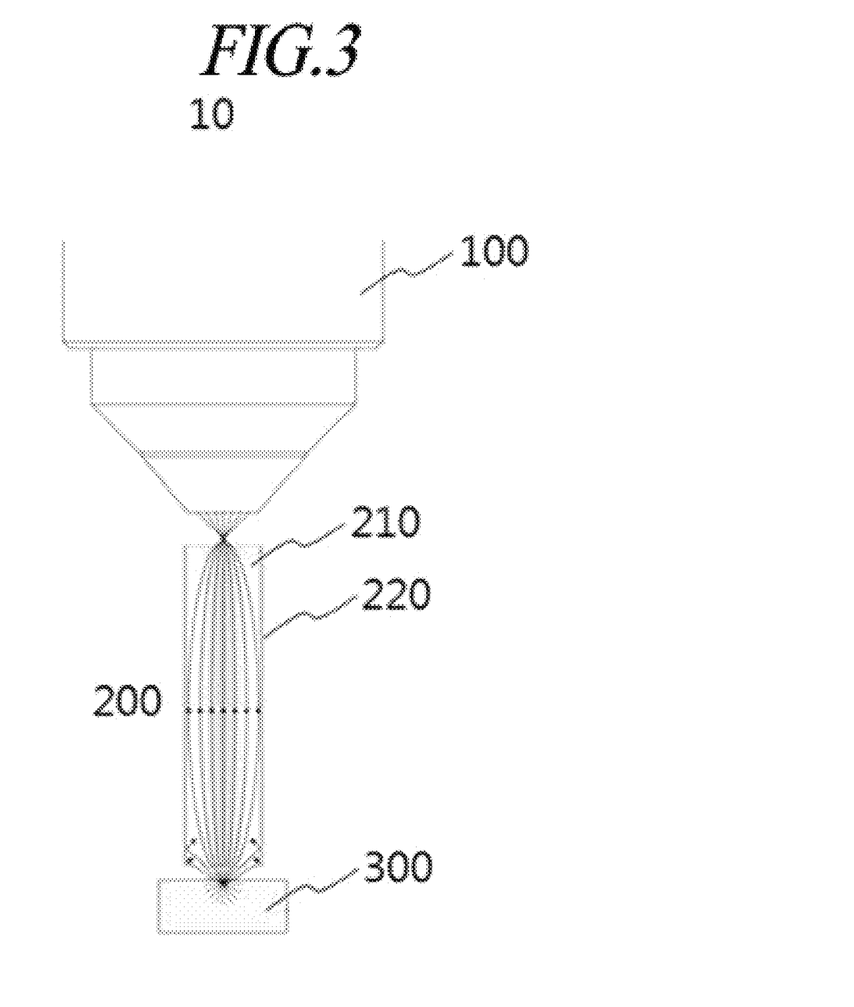
FIG. 3 is a schematic diagram illustrating a multi-photon endoscopy according to an embodiment.

FIG. 3 is a schematic diagram illustrating a multi-photon endoscopy according to an embodiment. Referring to FIG. 3, the multi-photon endoscopy 10 according to the embodiment includes a miniature endoscopic probe 200 and a multi-photon microscopy 100, and the miniature endoscopic probe 200 may include a gradient index (GRIN) lens 210 and a reflective waveguide 220.

According to an embodiment, the miniature endoscopic probe 200 may be fixed and coupled onto a focal plane of the multi-photon microscopy 100, but is not limited thereto.

According to an embodiment, the multi-photon endoscopy 10 may further include one selected from the group consisting of a non-descanned detector (NDD), a femtosecond laser, a galvo-scanner, and combinations thereof, but is not limited thereto.

According to the embodiment, the multi-photon microscopy 100 includes an objective lens (not illustrated), and the objective lens (not illustrated) may have a larger numerical aperture (NA) than the endoscopic probe 200, but is not limited thereto.

According to an embodiment, the objective lens (not illustrated) may have a numerical aperture of 0.2 to 1.5, but is not limited thereto.

According to an embodiment, the miniature endoscopic probe 200 may have a numerical aperture of 0.17 to 0.8, but is not limited thereto.

A signal transmitted through the miniature endoscopic probe may be a signal in a unique numerical aperture (0.2 to 1.5) transmitted according to a type of miniature endoscopic probe. In this case, in order to accept the signal of the miniature endoscopic probe without loss, the objective lens needs to have at least the same or larger numerical aperture as or than the miniature endoscopic probe.

Hereinafter, the present disclosure will be described in more detail with reference to the following Examples, but the following Examples are only for illustrative purposes and are not intended to limit the scope of the present disclosure.

Example

First, a phantom sample was prepared. For a fluorescent sample, rhodamine B (208108, Sigma Aldrich) was dissolved in 0.1 mM distilled water and 100 nm of fluorescent beads (F8801, Invitrogen) were diluted at 1:1000 in a 1% agarose gel. In the case of a second harmonic generation (SHG) sample, barium titanite (83689, Sigma Aldrich) was mixed with a solution of polydimethylsiloxane (PDMS; Sylgard 184, Sigma-Aldrich) containing 10% w/w of a curing agent. After particles were dispersed, the mixture was incubated at a constant temperature in a vacuum chamber for 1 hour to remove bubbles and then solidified at 70° C. for 2 hours.

Next, 8-week-old male transgenic mice (Thy1-YFP-H, Jackson Laboratory) and male C57B6 mice were used for brain and muscle samples, respectively. After deep anesthesia by intraperitoneal injection of 1 mg/g urethane, mice were perfused epidurally with physiological saline and 4% paraformaldehyde. Fresh brain and muscle tissues were extracted and the brain was sliced at a thickness of 200 μm with a vibratome (VT1000S, Leica). All animal experiments were conducted according to institutional guidelines and approved by the animal experiment subcommittee of the Sungkyunkwan University.

Subsequently, a miniature endoscopic probe including a GRIN lens having a reflective waveguide was manufactured. The bottom and top surfaces were protected with a polyimide tape to coat only the side surface of the GRIN lens. After sputtering deposition at 10 mTorr and 150 W for 16 minutes, the miniature endoscopic probe was completely covered with a silver thin film having a thickness of 200 nm or more. In order to further protect the silver thin film, a thin chromium layer was further deposited at 6 mTorr and 200 W for 8 minutes. After the deposition was completed, the polyimide tape was separated.

Subsequently, in consideration of the design of the miniature endoscopic probe, a 25×, 1.1 NA water immersion objective lens was selected. Since a numerical aperture of the objective lens is greater than or equal to the numerical aperture of the probe, a signal generated by the probe may be collected without loss. The emitted light was collected by a low-pass dichroic mirror with a cutoff at 700 nm and captured by a non-descanned detector consisting of a four-channel GaAsP photomultiplier tube.

Next, a multi-photon endoscopy (IntraVital, Bruker) included a femtosecond laser (Chameleon Vision II, Coherent) with a pre chirping unit, a beam scanner (6215H, CambridgeTech), a non-descanned detector consisting of a four-channel GaAsP photomultiplier tube, and a water immersion objective lens (25×, 1.1 NA; Nikon). A singlet GRIN lens-based probe (a diameter of 1 mm, a length of 4.38 mm, and an operating distance of 0.25 nm underwater; GrinTech) attached a proximal surface to a cover slip #1 using an optical adhesive (NOA81, Norland Products) and then fixed the proximal surface with a triaxial micrometer. The proximal surface of the miniature endoscopic probe was positioned on a focal plane of the multi-photon microscopy. The sample was positioned using a triaxial moving stage.

Subsequently, ImageJ (NIH) and Matlab (Mathworks) were used for image quantification, and Prism (Graphpad) was used for statistical analysis. Unless indicated otherwise, data was indicated as a mean±standard error or a box-whisker plot. Groups were compared with each other using either unpaired or paired t-test and considered statistically significant p-values of 0.05 or less.

Comparative Example

In order to confirm how the reflective waveguide affected the characteristics of the miniature endoscopic probe and the multi-photon endoscopy as the biggest characteristic, a miniature endoscopic probe of Comparative Example was manufactured. The miniature endoscopic probe was manufactured in the same manner as Example, and a general GRIN lens was used instead of the GRIN lens with the reflective waveguide of Example.

Experimental Example

FIGS. 4A to 4D are photographs and graphs showing collection efficiency results using the endoscopic probe s according to Example of the present disclosure and Comparative Example.

Referring to FIGS. 4A to 4D, the collection efficiencies were compared with each other using a rhodamine B solution that emitted red fluorescence collected at 570 nm to 640 nm. To make conditions of living tissue imaging of Example and Comparative Example similar, the side surface of the miniature endoscopic probe of Comparative Example was covered with a mixture of 0.1% alumina and polydimethylsiloxane (n≈1.4).

In addition, the fluorescent solution was immersed in a tip of the miniature endoscopic probe of Comparative Example or Example, and the fluorescence intensity was measured at the same excitation intensity and 2.5 mW and 840 nm measured at a rear aperture of the objective lens. The fluorescence image through the multi-photon endoscopy showed a typical contour that was decreased radially due to off-axis optical aberrations. In the case of using the miniature endoscopic probe of Example, a phenomenon in which the intensity of the fluorescence signal was increased two times or more larger than the case of using the miniature image relay endoscopy probe of Comparative Example may be confirmed by fluorescence dye imaging.

Figure 4:
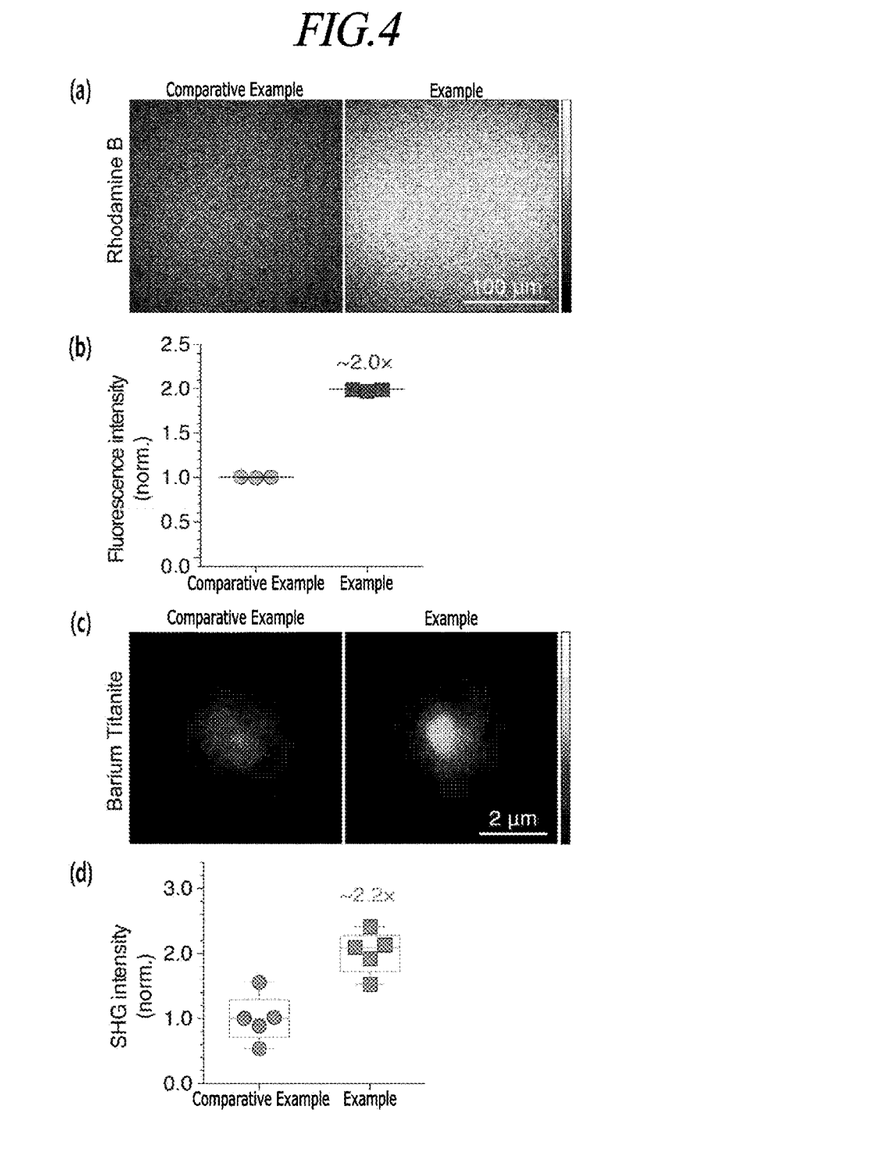
FIGS. 4A to 4D are photographs and graphs showing collection efficiency results using miniature endoscopic probe according to Example of the present disclosure and Comparative Example.

Referring to FIGS. 4C and 4D, barium titanite ($BaTIO_3$) nanoparticles instead of rhodamine B were experimented. The $BaTIO_3$ nanoparticles efficiently produced second harmonic generation (SHG) emission which was constant at half the fundamental wavelength and strong in directionality. Although there was individual variability in the second harmonic generation (SHG) intensity between the $BaTIO_3$ nanoparticles, it can be seen that the miniature endoscopic probe of Example had the collection results on averagely two times brighter than the miniature endoscopic probe of Comparative Example. In FIGS. 4A to 4D, it can be seen that the miniature endoscopic probe of Example has been improved in the second harmonic generation (SHG) and the fluorescence signal intensity about twice larger than the miniature endoscopic probe of Comparative Example.

FIGS. 5A to 5D are photographs and graphs showing collection efficiency results of applying the miniature endoscopic probe to living tissue observation according to Example of the present disclosure and Comparative Example. Following the theoretical performance calculation and simulation of FIGS. 4A to 4D, FIGS. 5A to 5D were experimental results of how much performance is improved when photographing a living tissue.

Figure 5:
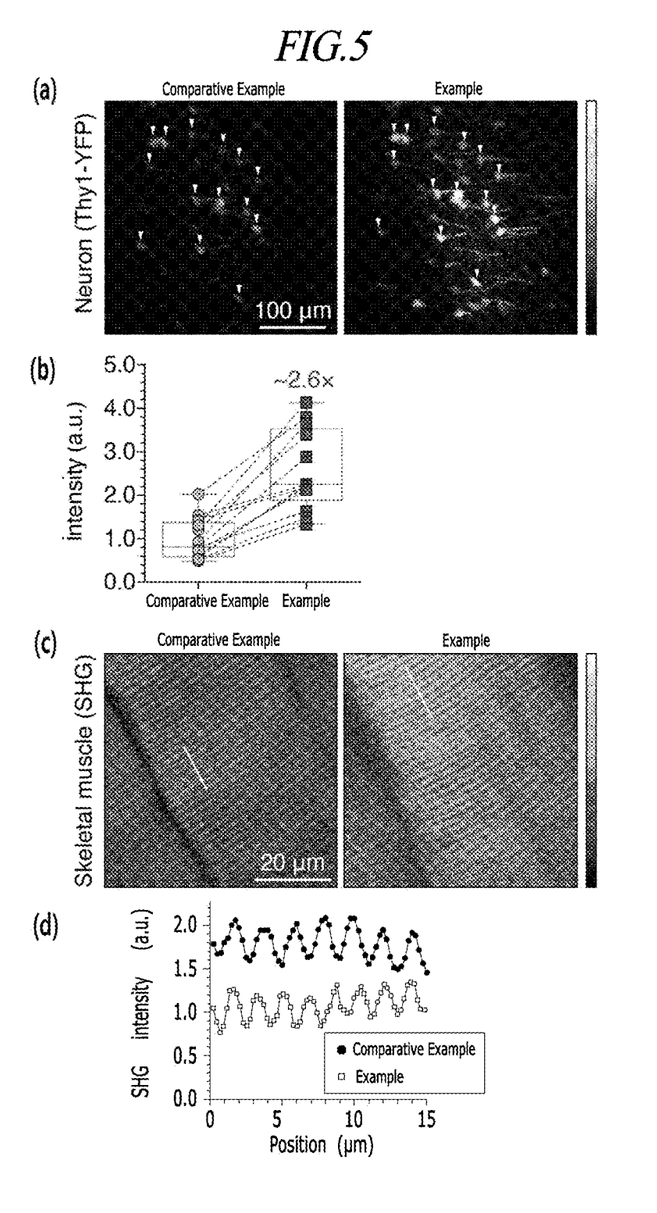
FIGS. 5A to 5D are photographs and graphs showing collection efficiency results of applying miniature endoscopic probe to living tissue observation according to Example of the present disclosure and Comparative Example.

Referring to FIGS. 5A and 5B, in order to experiment biological validity, the miniature endoscopic probe of Example and Comparative Example were compared with each other on fluorescent reporter mice (Thy1-YFP-H) expressing a yellow-fluorescent protein in excitatory neurons. Cortical layers of the coronal sections were imaged on a z-stack with an axial spacing of 2 µm by the miniature endoscopic probe of Example and Comparative Example. As expected in the phantom study, the miniature endoscopic probe of Example had fluorescence intensity 2.6 times larger than the miniature endoscopic probe of Comparative Example in fluorescent neurons, and more detailed tissue structure may be observed.

Referring to FIGS. 5C and 5D, it can be seen that in the miniature endoscopic probe of Example, the signal intensity of the second harmonic generation (SHG) emission measured in the muscle tissue of the rat thigh is also improved about twice larger than the miniature endoscopic probe of Comparative Example. As these results, it can be seen that the miniature endoscopic probe of Example provides immediate and practical utility in a biological research. For example, twice higher collection efficiency may provide an improved signal-to-noise ratio within 40% or twice more rapid acquisition at constant excitation power. By exploiting this, the same imaging quality may be obtained at an excitation output reduced to 40% and may suppress negative changes such as photo-toxicity and photo-bleaching effects.

The scope of the present disclosure is represented by claims to be described below rather than the detailed description, and it is to be interpreted that the meaning and scope of the claims and all the changes or modified forms derived from the equivalents thereof come within the scope of the present disclosure.

What is claimed is:

1. A miniature endoscopic probe comprising:
    a gradient index lens (GRIN lens) comprising a reflective waveguide; and
    a protective layer disposed on the reflective waveguide,
    wherein the reflective waveguide is disposed on a side surface of the GRIN lens, and
    wherein the protective layer comprises a polymer coating.

2. The miniature endoscopic probe of claim 1, wherein the reflective waveguide is formed by light reflection coating on the side surface of the GRIN lens.

3. The miniature endoscopic probe of claim 2, wherein the reflective waveguide comprises a metal selected from the group consisting of silver, gold, aluminum, tin, copper, brass, bronze, molybdenum, chromium, rhodium, platinum and combinations thereof or a dielectric material selected from the group consisting of $SiO_2$, $TiO_2$, $Ta_2O_5$, $MgF_2$, $Al_2O_3$ and combinations thereof.

4. The miniature endoscopic probe of claim 2, wherein the light reflection coating is performed by a method selected from the group consisting of vacuum deposition, sputter deposition, lithography, solution-based reductive coating, and combinations thereof.

5. The miniature endoscopic probe of claim 1, wherein the polymer coating comprises a parylene coating.

6. A multi-photon endoscope comprising:
    a miniature endoscopic probe comprising a gradient index lens (GRIN lens) comprising a reflective waveguide; and
    a multi-photon microscope,
    wherein the reflective waveguide is disposed on a side surface of the GRIN lens.

7. The multi-photon endoscope of claim 6, wherein the miniature endoscopic probe is fixed and coupled onto a focal plane of the multi-photon microscope.

8. The multi-photon endoscope of claim 6, further comprising:
    one selected from the group consisting of a non-descanned detector, a femtosecond pulsed laser, a galvo-scanner, and combinations thereof.

9. The multi-photon endoscope of claim 6, wherein the multi-photon microscope comprises an objective lens, and the objective lens has a numerical aperture NA larger than that of the miniature endoscopic probe.

10. The multi-photon endoscope of claim 9, wherein the objective lens has a numerical aperture of 0.2 to 1.5.

11. The multi-photon endoscope of claim 9, wherein the miniature endoscopic probe has a numerical aperture of 0.17 to 0.8.

12. The multi-photon endoscope of claim 6, wherein the reflective waveguide is formed by light reflection coating on the side surface of the GRIN lens.

13. The multi-photon endoscope of claim 12, wherein the reflective waveguide comprises a metal selected from the group consisting of silver, gold, aluminum, tin, copper, brass, bronze, molybdenum, chromium, rhodium, platinum and combinations thereof or a dielectric material selected from the group consisting of $SiO_2$, $TiO_2$, $Ta_2O_5$, $MgF_2$, $Al_2O_3$ and combinations thereof.

14. The multi-photon endoscope of claim 12, wherein the light reflection coating is performed by a method selected from the group consisting of vacuum deposition, sputter deposition, lithography, solution-based reductive coating, and combinations thereof.

15. The multi-photon endoscope of claim 6, further comprising a protective layer disposed on the reflective waveguide.

16. The miniature endoscopic probe of claim 15, wherein the protective layer comprises an alloy steel tube.

17. The miniature endoscopic probe of claim 16, wherein the alloy steel tube comprises a steel selected from the group consisting of stainless steel, chromium steel, nickel steel, nickel-chromium steel, chromium-molybdenum steel, manganese steel, chromium-vanadium steel, tungsten steel and combinations thereof.

18. The multi-photon endoscope of claim 15, wherein the protective layer is formed by polymer coating.

19. The multi-photon endoscope of claim 18, wherein the polymer coating comprises parylene coating.

* * * * *